United States Patent [19]
Harada et al.

[11] Patent Number: 5,892,089
[45] Date of Patent: Apr. 6, 1999

[54] PROCESS FOR PREPARING DIARYL CARBONATE

[75] Inventors: Katsumasa Harada; Ryoji Sugise; Koichi Kashiwagi; Yoichi Imbe; Takashi Doi; Keigo Nishihira; Shuji Tanaka; Hirofumi Ii, all of Yamaguchi, Japan

[73] Assignee: Ube Industries, Ltd., Yamaguchi, Japan

[21] Appl. No.: 944,231

[22] Filed: Oct. 6, 1997

[30] Foreign Application Priority Data

Oct. 4, 1996 [JP] Japan ................................. 8-264763
Oct. 4, 1996 [JP] Japan ................................. 8-264764

[51] Int. Cl.$^6$ .................................................. C07C 68/00
[52] U.S. Cl. ............................................................. 558/274
[58] Field of Search ............................................... 558/274

[56] References Cited

U.S. PATENT DOCUMENTS 5,648,510  7/1997  Harada et al. ........................... 558/274

Primary Examiner—Michael G. Ambrose
Attorney, Agent, or Firm—McAulay Nissen Goldberg Kiel & Hand, LLP

[57] ABSTRACT

A process for preparing a diaryl carbonate from a diaryl oxalate in a liquid phase by decarbonylation is conducted by the steps of:

1) performing a decarbonylation reaction of a diaryl oxalate in the presence of an organic phosphorus compound catalyst to give a reaction mixture of a diaryl carbonate and the organic phosphorus compound catalyst;

2) recovering the diaryl carbonate from the reaction mixture; and 3) performing a decarbonylation reaction of a diaryl oxalate in the presence of the reaction mixture from which the diaryl carbonate has been recovered and to which a halogen atom-containing compound is added, to give a reaction mixture of a diaryl carbonate and the organic phosphorus compound catalyst.

11 Claims, 1 Drawing Sheet

PROCESS FOR PREPARING DIARYL CARBONATE

FIELD OF THE INVENTION

The present invention relates to a process for preparing a diaryl carbonate from a diaryl oxalate in a liquid phase by decarbonylation. The diaryl carbonate is favorably employable for producing a polycarbonate.

BACKGROUND OF THE INVENTION

It is known that a diaryl carbonate can be prepared from a diaryl oxalate by decarbonylation. The known process, however, is not favorably employable in industry because the reaction rate is very slow and the yield and selectivity are low.

Yuki Gosei Kagaku Kyokaishi (Journal of Synthetic Organic Chemistry, Japan), Vol.5, No.4–9, Report 47, pp. 70–71(1948) teaches a reaction in which diphenyl oxalate is heated to release carbon monoxide to give diphenyl carbonate. This report describes neither yield nor selectivity. According to a trace experiment of the experiment of this report, only a small amount of diphenyl carbonate is produced.

U.S. Pat. No. 4,544,507 describes that the carbonic acid dialkyl ester, i.e., dialkyl carbonate, can be prepared by heating a dialkyl oxalate in a liquid phase at 50°–150° C. in the presence of an alcolate catalyst. In the working example of the Patent publication, the diphenyl oxalate is heated in the presence of a potassium phenoxide catalyst only to give mainly the diphenyl oxalate, namely, the starting compound.

SUMMARY OF THE INVENTION

It is an object of the present invention to provide a process for continuously preparing a diaryl carbonate from a diaryl oxalate by decarbonylation in an increased yield with a high selectivity.

It is another object of the invention to provide a process for continuously preparing a diaryl carbonate from a diaryl oxalate by decarbonylation in an increased yield with a high selectivity utilizing a catalyst which can be recovered and employed repeatedly.

The present invention resides in a process for preparing a diaryl carbonate from a diaryl oxalate in liquid phase by decarbonylation which comprises the steps of:

1) performing a decarbonylation reaction of a diaryl oxalate in the presence of an organic phosphorus compound catalyst to give a reaction mixture comprising a diaryl carbonate and the organic phosphorus compound catalyst;

2) recovering the diaryl carbonate from the reaction mixture; and 3) performing a decarbonylation reaction of a diaryl oxalate in the presence of the reaction mixture from which the diaryl carbonate has been recovered and to which a halogen atom-containing compound is added, to give a reaction mixture comprising a diaryl carbonate and the organic phosphorus compound catalyst.

In the process of the invention, the steps 2) and 3) are preferably repeated batchwise or continuously in combination.

The organic phosphorus compound catalyst preferably comprises a compound having a trivalent or pentavalent phosphorus atom and at least one carbon-phosphorus bonding. More preferably, the catalyst comprises a compound selected from the group consisting of an organic phosphonium compound, a phosphine, a phosphine dihalide, and a phosphine oxide. Specifically preferred is that the catalyst comprises a tetraarylphosphonium salt, a triarylphosphine, a triaryiphosphine dihalide, or a triaryiphasphine oxide. Also specifically preferred is that the catalyst comprises a tetraarylphosphonium halide or a tetraarylphosphonium hydrogen dihalide.

The halogen atom-containing compound preferably is an organic halogen atom-containing compound having a chemical structure in which a halogen atom is bonded to a carbon atom having thereon no double bond other than =O, or an inorganic halogen atom-containing compound selected from the group consisting of a halide of phosphorus, a halide of sulfur, a hydrogen halide, and a halogen. The most preferred halogen atom-containing compound is a chlorine-containing compound.

In the case that the organic phosphorous compound catalyst comprises an organic phosphonium salt, the reaction mixture from which the diaryl carbonate has been recovered is preferably treated with an aqueous medium to recover the organic phosphonium salt; and the recovered organic phosphonium salt is employed in the step 1) as the catalyst. The recovery of the organic phosphonium salt can be performed after the steps 2) and 3) are repeated in combination.

BRIEF DESCRIPTION OF DRAWINGS

Each of FIGS. 1 to 2 illustrates a flow sheet which is employable for performing the process of the invention.

DETAILED DESCRIPTION OF THE INVENTION

The decarbonylation process for preparing a diaryl carbonate from a diaryl oxalate can be illustrated as follows:

wherein Ar stands for an unsubstituted or substituted aryl group.

The aryl group of the diaryl oxalate can be: (1) a phenyl group; (2) a phenyl group having one or more substituents such as an alkyl group having 1 to 12 carbon atoms (e.g., methyl and ethyl), an alkoxy group having 1 to 12 carbon atoms (e.g., methoxy and ethoxy), a halogen atoms (e.g., fluorine and chlorine), and nitro; or (3) a naphthyl group. Preferred is a phenyl group.

The phenyl group having one or more substituents, that is named "a substituted phenyl group", may be in the form of one of various isomers. Examples of the isomers include 2-(or 3-, or 4-)alkylphenyl, such as 2-(or 3-, or 4-)methylphenyl, or 2-(or 3-, or 4-)ethylphenyl; 2-(or 3-, or 4-)alkoxyphenyl, such as 2-(or 3-, or 4-)-methoxyphenyl, or 2-(or 3-, or 4-)ethoxyphenyl; 2-(or 3-, or 4-)halogenated phenyl, such as 2-(or 3-, or 4-)fluorophenyl, or 2-(or 3-, or 4-)chlorophenyl; and 2-(or 3-, or 4-)nitorophenyl.

Examples of the diaryl oxalates include diphenyl oxalate, bis(2-methylphenyl)oxalate, bis(3-methylphenyl)oxalate, bis(4-methylphenyl)oxalate, bis(2-chlorophenyl)oxalate, bis(3-chlorophenyl)oxalate, bis(4-chlorophenyl)oxalate, bis(2-nitrophenyl)oxalate, bis(3-nitrophenyl)oxalate, and bis(4-nitrophenyl)oxalate. Most preferred is diphenyl oxalate.

In the decarbonylation process of the invention, the decarbonylation catalyst preferably is an organic phosphorus compound having a trivalent or pentavalent phosphorus atom, and having at least one carbon-phosphorus bonding.

Preferred are organic phosphorus compounds having three or more carbon-phosphorus bondings. Preferred organic phosphorus compounds are a phosphonium salt having the following formula (A), a phosphine having the following formula (B), a phosphine dihalide having the following formula (C), and a phosphine oxide having the following formula (D):

Formula (A):
$$R^2-\underset{\underset{R^3}{|}}{\overset{\overset{R^1}{|}}{P^+}}-R^4 \cdot X^-$$

Formula (B):
$$R^6-\underset{\underset{R^7}{|}}{\overset{\overset{R^5}{|}}{P}}$$

Formula (C):
$$R^9-\underset{\underset{R^{10}}{\diagup}}{\overset{\overset{R^8}{\diagdown}}{P}}\underset{\underset{Y^2}{\diagdown}}{\overset{\overset{Y^1}{\diagup}}{}}$$

Formula (D):
$$R^{12}-\underset{\underset{R^{13}}{|}}{\overset{\overset{R^{11}}{|}}{P}}=O$$

Detailed descriptions are given below for the phosphonium salt of formula (A), the phosphine of formula (B), the phosphine dihalide of formula (C), and the phosphine oxide of formula (D).

(A) Phosphonium Salt of the formula (A)

The phosphonium salt can be represented by the above formula (A), wherein each of $R^1$, $R^2$, $R^3$ and $R^4$ independently represents an aryl group of 6 to 10 carbon atoms, an alkyl group of 1 to 16 carbon atoms, an aralkyl group of 7 to 22 carbon atoms, an aryloxy group of 6 to 10 carbon atoms, or a heterocyclic group of 4 to 16 carbon atoms, and X represents a counter ion of the phosphonium ion. Any two of $R^1$, $R^2$, $R^3$ and $R^4$ may be combined to form a ring having the phosphorus atom as its ring member.

The aryl group is described in more detail. The aryl group can be a phenyl or naphthyl group. The phenyl or naphthyl group can have one or more substituents in any positions. Examples of the substituents include alkyl of 1 to 15 carbon atoms, preferably of 1 to 12 carbon atoms (e.g., methyl, ethyl, n-propyl, isopropyl, n-butyl, isobutyl, sec-butyl, or tert-butyl), alkoxy of 1 to 15 carbon atoms, preferably of 1 to 12 carbon atoms (e.g., methoxy, ethoxy, n-propoxy, isopropoxy, n-butoxy, isobutoxy, sec-butoxy, or tert-butoxy), alkoxycarbonyl of 2 to 12 carbon atoms, preferably of 2 to 8 carbon atoms (e.g., methoxycarbonyl or ethoxycarbonyl), aryl (e.g., phenyl), amino such as N,N-dialkyl-substituted amino (e.g., N,N-dimethylamino), cyano, nitro, and halo (e.g., fluoro, chloro, or bromo).

The alkyl group is described in more detail. The alkyl group can have 1 to 16 carbon atoms. Examples of the alkyl group include methyl, ethyl, n-propyl, isopropyl, n-butyl, isobutyl, sec-butyl, or tert-butyl. The alkyl group can have one or more substituents in any positions. Examples of the substituents are the same as those described for the substituents of the aryl group.

The aralkyl group is described in more detail. The aralkyl group can have 7 to 22 carbon atoms. Examples of the aralkyl group include benzyl, phenethyl and naphthylmethyl. The aralkyl group can have one or more substituents in any positions. Examples of the substituents are the same as those described for the substituents of the aryl group.

The aryloxy group is described in more detail. The aryloxy group can be a phenoxy or naphthoxy group. The aryloxy group can have one or more substituents in any positions. Examples of the substituents are the same as those described for the substituents of the aryl group.

The heterocyclic group is described in more detail. The heterocyclic group can have 4 to 16 carbon atoms, and at least one hetero atom such as oxygen, sulfur, or nitrogen. Examples of the heterocyclic group include thienyl, furyl, and pyridyl. The heterocyclic group can have one or more substituents in any positions. Examples of the substituents are the same as those described for the substituents of the aryl group.

The groups of $R^1$, $R^2$, $R^3$ and $R^4$ of the phosphonium salt can be the same or different from each other. For instance, all of the groups of $R^1$, $R^2$, $R^3$ and $R^4$ are aryl groups in one phosphonium salt, that is, a tetraarylphosphonium salt. Three of the groups are aryl groups and other one is another group, that is, a triarylphosphonium salt. Two of the groups are aryl groups and other two are other groups, that is, a diarylphosphonium salt. Only one of the groups is an aryl group and other three are other groups, that is, an arylphosphonium salt. All of the groups of $R^1$, $R^2$, $R^3$ and $R^4$ are other than the aryl groups. Preferred are the tetraarylphosphonium salt and an arylphosphonium salt in which three of the groups of $R^1$, $R^2$, $R^3$ and $R^4$ are aryl groups and other one is a heterocyclic group.

The counter ion ($X^-$) can be a halide ion (e.g., chloride ion, bromide ion, or iodide ion), a hydrogen dihalide ion (e.g., hydrogen dichloride ion, hydrogen dibromide ion, hydrogen diiodide ion, or hydrogen bromide chloride ion), a halogen acid ion (e.g., chlorate ion, bromate ion, or iodate ion), a per-halogen acid ion (e.g., perchlorate ion, perbromate ion, or periodate ion), an aliphatic carboxylate ion (e.g., acetate ion, trifluoroacetate ion, or propionate ion), an aromatic carboxylate ion (e.g., benzoate ion, or α- or β-naphthalenecarboxylate ion), an aromatic hydroxyl ion (e.g., phenoxide ion), an inorganic acid ion (e.g., sulfate ion, sulfite ion, phosphate ion, phosphite ion, borate ion, hydrogenborate ion, cyanate ion, thiocyanate ion, or fluoroborate ion), an alkylsulfonate or alkylsulfinate ion having an alkyl group of 1 to 16 carbon atoms (e.g., methyl, ethyl, n-propyl, or isopropyl), an arylsulfonate or arylsulfinate ion having an aryl group (e.g., phenyl, p-tolyl, or p-nitorophenyl), a tetraalkylborate ion having an alkyl group of 1 to 10 carbon atoms (e.g., tetramethylborate ion, or tetraethylborate ion), or a tetraarylborate ion (e.g., tetraphenylborate ion, or tetrakisp-fluorophenylborate ion). Examples of preferred counter ions ($X^-$) include halide ions such as chloride ion, bromide ion and iodide ion, and hydrogen dihalide ions such as hydrogen dichloride ion, hydrogen dibromide ion, hydrogen diiodide ion, and hydrogen bromide chloride ion. Most preferred are chloride ion and hydrogen dichloride ion.

Concrete examples of the preferred phosphonium salts of the formula (A) are described below.

(1) Phosphonium salt in which all of $R^1$, $R^2$, $R^3$ and $R^4$ are aryl groups and $X^-$ is a halide ion Examples are tetraphenylphosphonium chloride, tetraphenylphosphonium bromide, tetraphenylphosphonium iodide, tetrakis(p-chlorophenyl)phosphonium chloride, tetrakis(p-fluorophenyl)phosphonium chloride, tetrakis(p-tolyl) phosphonium chloride, p-chlorophenyltriphenylphosphonium chloride, p-chlorophenyltriphenylphosphonium bromide, p-chlorophenyltriphenylphosphonium iodide, p-tolyltriphenylphosphonium chloride, p-tolyltriphenylphosphonium bromide, p-tolyltriphenylphosphonium iodide, m-trifluoromethylphenyltriphenylphosphonium chloride, p-biphenyltriphenylphosphonium chloride, m-methoxyphenyltriphenylphosphonium chloride, p-methoxyphenyltriphenylphosphonium chloride, p-ethoxyphenyltriphenylphosphonium chloride, p-ethoxyphenyltriphenylphosphonium bromide, p-ethoxyphenyltriphenylphosphonium iodide, p-dimethylaminophenyltriphenylphosphonium chloride, p-ethoxycarbonylphenyltriphenylphosphonium chloride, m-cyanophenyltriphenylphosphonium chloride, and 1-naphthyltriphenylphosphonium chloride. Most preferred is tetraphenylphosphonium chloride.

(2) Phosphonium salt in which all of $R^1$, $R^2$, $R^3$ and $R^4$ are aryl groups and $X^-$ is a hydrogen dihalide ion Examples are tetraphenylphosphonium hydrogen dichloride, tetraphenylphosphonium hydrogen dibromide, tetraphenylphosphonium hydrogen diiodide, and tetraphenylphosphonium hydrogen bromide chloride. Most preferred is tetraphenylphosphonium hydrogen dichloride.

(3) Phosphonium salt in which all of $R^1$, $R^2$, $R^3$ and $R^4$ are aryl groups and $X^-$ is an aliphatic or aromatic carboxylate ion Examples are tetraphenylphosphonium acetate, p-chlorophenyltriphenylphosphonium acetate, p-ethoxyphenyltriphenylphosphonium acetate, p-tolyltriphenylphosphonium acetate, tetraphenylphosphonium trifluoroacetate, and tetraphenylphosphonium benzoate.

(4) Phosphonium salt in which all of $R^1$, $R^2$, $R^3$ and $R^4$ are aryl groups and $X^-$ is fluoroborate ion Examples are tetraphenylphosphonium fluoroborate, p-chlorophenyltriphenylphosphonium fluoroborate, p-ethoxyphenyltriphenylphosphonium fluoroborate, and p-tolyltriphenylphosphonium fluoroborate.

(5) Phosphonium salt in which all of $R^1$, $R^2$, $R^3$ and $R^4$ are aryl groups and $X^-$ is thiocyanide ion An example is tetraphenylphosphonium thiocyanide.

(6) Phosphonium salt in which all of $R^1$, $R^2$, $R^3$ and $R^4$ are aryl groups and $X^-$ is an aromatic hydroxyl ion An example is tetraphenylphosphonium phenoxide.

(7) Phosphonium salt in which three of $R^1$, $R^2$, $R^3$ and $R^4$ are aryl groups, one is an alkyl group, and $X^-$ is a halide ion Examples are methyltriphenylphosphonium chloride, methyltriphenylphosphonium bromide, methyltriphoylphosphonium iodide, ethyltriphenylphosphonium chloride, ethyltriphenylphosphonium bromide, ethyltriphenylphosphonium iodide, n-propyltriphenylphosphonium chloride, n-propyltriphenylphosphonium bromide, n-propyltriphenylphosphonium iodide, isopropyltriphenylphosphonium chloride, isopropyltriphenylphosphonium bromide, n-dodecyltriphenylphosphonium chloride, n-dodecyltriphenylphosphonium bromide, chloromethyltriphenylphosphonium chloride, methyltris(m-chlorophenyl) phosphonium chloride, methyltris(m-chlorophenyl) phosphonium bromide, ethyltris(m-chlorophenyl) phosphonium chloride, and ethyltris(m-chlorophenyl) phosphonium bromide.

(8) Phosphonium salt in which three of $R^1$, $R^2$, $R^3$ and $R^4$ are aryl groups, one is an aralkyl group, and $X^-$ is a halide ion Examples are benzyltriphenylphosphonium chloride, p-fluorobenzyltriphenylphosphonium chloride, p-fluorobenzyltriphenylphosphonium bromide, 2,4-dichlorobenzyltriphenylphosphonium chloride, 2,4-dichlorobenzyltriphenylphosphonium bromide, p-n-butoxybenzyltriphenylphosphonium chloride, p-n-butoxybenzyltriphenylphosphonium bromide, 2-naphthylmethyltriphenylphosphonium chloride, 2-naphthylmethyltriphenylphosphonium bromide, 9-fluorenyltriphenylphosphonium chloride, and 9-fluorenyltriphenylphosphonium bromide.

(9) Phosphonium salt in which three of $R^1$, $R^2$, $R^3$ and $R^4$ are aryl groups, one is a heterocyclic group, and $X^-$ is a halide ion An example is 2-thiophenetriphenylphosphonium chloride.

(10) Phosphonium salt in which three of $R^1$, $R^2$, $R^3$ and $R^4$ are aryl groups, one is an aryloxy group, and $X^-$ is a halide ion An example is phenoxytriphenylphosphonium chloride.

(11) Phosphonium salt in which three of $R^1$, $R^2$, $R^3$ and $R^4$ are aryl groups, one is an alkyl group, and $X^-$ is an aliphatic carboxylate ion Examples are methyltriphenylphosphonium acetate, ethyltriphenylphosphonium acetate, and n-propyltriphenylphosphonium acetate.

(12) Phosphonium salt in which three of $R^1$, $R^2$, $R^3$ and $R^4$ are aryl groups, one is an alkyl group, and $X^-$ is a fluoroborate ion Examples are methyltriphenylphosphonium fluoroborate, ethyltriphenylphosphonium fluoroborate, and n-propyltriphenylphosphonium fluoroborate.

(13) Phosphonium salt in which two of $R^1$, $R^2$, $R^3$ and $R^4$ are aryl groups, other two are other groups, and $X^-$ is a halide ion Examples are dimethyldiphenylphosphonium chloride, diethyldiphenylphosphonium chloride, dimethyldiphenylphosphonium bromide, and diethyldiphenylphosphonium bromide.

(14) Phosphonium salt in which one of $R^1$, $R^2$, $R^3$ and $R^4$ are aryl groups, other three are other groups, and $X^-$ is a halide ion Examples are diethylmethylphenylphosphonium chloride, and diethylmethylphenylphosphonium bromide.

(15) Phosphonium salt in which none of $R^1$, $R^2$, $R^3$ and $R^4$ are aryl groups, and $X^-$ is a halide ion Examples are tetra-n-butylphosphonium chloride, and tetra-n-butylphosphonium bromide.

Some of the above-mentioned phosphonium salts are known and available on market. Other phosphonium salts can be prepared by the processes set forth in Bull. Chem. Soc. Jpn., 56, 2869 (1983) and J. Am. Chem. Soc., 70, 737 (1948), or processes similar to those described in these publications.

For instance, the tetraarylphosphonium chloride can be prepared by reacting a triarylphosphine and an aryl halide (e.g., aryl iodide or aryl bromine) in the presence of a palladium acetate catalyst and treating the resulting tetraarylphosphonium iodide or bromide with an ion exchange resin (chloride type) to give the desired tetraarylphosphonium chloride. The produced tetraarylphosphonium chloride is preferably dried. For the drying, the tetraarylphosphonium chloride is preferably heated to 100° to 200° C. for 0.5 to 5 hours in a stream of a dry inert gas such as dry argon gas and then heated to 80° to 200° C. for 0.5 to 2 hours in a stream of a dry hydrogen chloride gas. The commercially available tetraarylphosphonium chloride is also preferred to be subjected to the above-mentioned process.

The tetraarylphosphonium salt having a counter ion other than halide ion can be prepared by reacting the above-obtained tetraarylphosphonium chloride with an alkali metal salt (e.g., sodium salt or potassium salt) or an ammonium salt of the desired counter ion, that is, ion exchange reaction. Other phosphonium salts other than the tetraaryl phosphonium salts can be prepared in the same manner or an analogous manner. These phosphonium salts are also preferred to be subjected to the drying treatment, in advance of its use as the catalyst.

(B) Phosphine of the formula (B)

The phosphine can be represented by the above formula (B), wherein each of $R^5$, $R^6$ and $R^7$ independently represents an aryl group, an alkyl group of 1 to 16 carbon atoms, an aralkyl group of 7 to 22 carbon atoms, or a heterocyclic group of 4 to 16 carbon atoms. Any two of $R^5$, $R^6$ and $R^7$ may be combined to form a ring having the phosphorus atom as its ring member.

Examples of the aryl group, alkyl group, aralkyl group and heterocyclic group are the same as those described for the phosphonium salt of the formula (A).

The groups of $R^5$, $R^6$ and $R^7$ of the phosphine can be the same or different from each other. For instance, all of the groups of $R^5$, $R^6$ and $R^7$ are aryl groups in one phosphine, that is, a triarylphosphine. Two of the groups are aryl groups and other one is another group, that is, a diarylphosphine. Only one of the groups is an aryl group and other two are other groups, that is, an arylphosphine. All of the groups of $R^5$, $R^6$ and $R^7$ are other than the aryl groups. Preferred is the phosphine in which all of the groups of $R^5$, $R^6$ and $R^7$ are aryl groups.

Concrete examples of the preferred phosphines of the formula (B) are described below.

(1) Phosphine in which all of $R^5$, $R^6$ and $R^7$ are aryl groups (i.e., triarylphosphine)

Examples are triphenylphosphine, tris(p-chlorophenyl) phosphine, tris(p-tolyl)phosphine, and α-naphthyl(phenyl)-p-methoxyphenylphosphine.

(2) Phosphine in which two of $R^5$, $R^6$ and $R^7$ are aryl groups and one is other group (i.e., diarylphosphine)

Examples are methyldiphenylphosphine and phenyl-(p-methoxyphenyl)methylphosphine.

(3) Phosphine in which one of $R^5$, $R^6$ and $R^7$ is an aryl group and other two are other groups (i.e., arylphosphine)

Examples are dimethyl(phenyl)phosphine and ethyl-(phenyl)-n-propylphosphine.

(4) Phosphine in which none of $R^5$, $R^6$ and $R^7$ are aryl groups

Examples are benzyl-(n-butyl)methylphosphine and tributylphosphine. An example of a phosphine in which any two of $R^5$, $R^6$ and $R^7$ are combined to form a ring having the phosphorus atom as its ring member is phenylbiphenylenephosphine.

(C) Phosphine Dihalide of the formula (C)

The phosphine dihalide can be represented by the above formula (C), wherein each of $R^8$, $R^9$ and $R^{10}$ independently represents an aryl group, an alkyl group of 1 to 16 carbon atoms, an aralkyl group of 7 to 22 carbon atoms, or a heterocyclic group of 4 to 16 carbon atoms, and each of $Y^1$ and $Y^2$ independently represents a halogen atom such as chlorine, bromine or iodine. Any two of $R^8$, $R^9$ and $R^{10}$ may be combined to form a ring having the phosphorus atom as its ring member.

Examples of the aryl group, alkyl group, aralkyl group and heterocyclic group are the same as those described for the phosphonium salt of the formula (A).

The groups of $R^8$, $R^9$ and $R^{10}$ of the phosphine dihalide can be the same or different from each other. For instance, all of the groups of $R^8$, $R^9$ and $R^{10}$ are aryl groups in one phosphine, that is, a triarylphosphine dihalide. Two of the groups are aryl groups and other one is another group, that is, a diarylphosphine dihalide. Only one of the groups is an aryl group and other two are other groups, that is, an arylphosphine dihalide. All of the groups of $R^8$, $R^9$ and $R^{10}$ are other than the aryl groups. Preferred is the phosphine dihalide in which all of the groups of $R^8$, $R^9$ and $R^{10}$ are aryl groups.

Concrete examples of the preferred phosphine dihalides of the formula (C) are triphenylphosphine dichloride, triphenylphosphine dibromide, and triphenylphosphine diiodide.

(D) Phosphine Oxide of the formula (D)

The phosphine oxide can be represented by the above formula (D), wherein each of $R^{11}$, $R^{12}$ and $R^{13}$ independently represents an aryl group, an alkyl group of 1 to 16 carbon atoms, an aralkyl group of 7 to 22 carbon atoms, or a heterocyclic group of 4 to 16 carbon atoms. Any two of $R^{11}$, $R^{12}$ and $R^{13}$ may be combined to form a ring having the phosphorus atom as its ring member.

Examples of the aryl group, alkyl group, aralkyl group and heterocyclic group are the same as those described for the phosphonium salt of the formula (A).

The groups of $R^{11}$, $R^{12}$ and $R^{13}$ of the phosphine oxide can be the same or different from each other. For instance, all of the groups of $R^{11}$, $R^{12}$ and $R^{13}$ are aryl groups in one phosphine, that is, a triarylphosphine oxide. Two of the groups are aryl groups and other one is another group, that is, a diarylphosphine oxide. Only one of the groups is an aryl group and other two are other groups, that is, an arylphosphine oxide. All of the groups of $R^{11}$, $R^{12}$ and $R^{13}$ are other than the aryl groups. Preferred is the phosphine oxide in which all of the groups of $R^{11}$, $R^{12}$ and $R^{13}$ are aryl groups.

Concrete examples of the preferred phosphine oxides of the formula (D) are described below.

(1) Phosphine oxide in which all of $R^{11}$, $R^{12}$ and $R^{13}$ are aryl groups (i.e., triarylphosphine oxide)

Examples are triphenylphosphine oxide, tris(p-chlorophenyl)phosphine oxide, tris(p-tolyl)phosphine oxide, and α-naphthyl(phenyl)-p-methoxyphenylphosphine oxide.

(2) Phosphine oxide in which two of $R^{11}$, $R^{12}$ and $R^{13}$ are aryl groups and one is other group (i.e., diarylphosphine oxide)

Examples are methyldiphenylphosphine oxide and phenyl-(p-methoxyphenyl)methylphosphine oxide.

(3) Phosphine oxide in which one of $R^{11}$, $R^{12}$ and $R^{13}$ is an aryl group and other two are other groups (i.e., aryl phosphine oxide)

Examples are dimethyl(phenyl)phosphine oxide and ethyl(phenyl)n-propylphosphine oxide.

(4) Phosphine oxide in which none of $R^{11}$, $R^{12}$ and $R^{13}$ are aryl groups Examples are benzyl-(n-butyl)methylphosphine oxide and tributylphosphine oxide. An example of a phosphine in which any two of $R^{11}$, $R^{12}$ and $R^{13}$ are combined to form a ring having the phosphorus atom as its ring member is phenylbiphenylenephosphine oxide.

Among the above-mentioned organic phosphorus compounds, tetraarylphosphonium halide, tetraarylphosphonium hydrogen dihalide, and triarylphosphine dihalide are preferred. Most preferred are tetraarylphosphonium chloride, tetraarylphosphonium hydrogen dichloride, and triarylphosphine dichloride. The organic phosphorus compound can be employed singly or in combination in the process of the present invention. The organic phosphorus compound can be dissolved or dispersed in the reaction medium.

The organic phosphorus compound can be employed in an amount of 0.001 to 50 mol. %, preferably 0.01 to 20 mol. %, based on the amount of diaryl oxalate (100 mol. %).

In the reaction for preparing a diaryl carbonate from a diaryl oxalate according to the invention, a halogen atom-containing compound can be incorporated. Particularly, in the cases where a phosphonium salt other than the phosphonium halide and phosphonium hydrogen dihalide are used as the phosphorus compound and where a phosphonium halide or a phosphonium hydrogen dihalide is used in a small amount, the incorporation of a halogen atom-containing compound is preferred. The halogen atom-containing compound preferably is a chlorine atom-containing compound or a bromine atom-containing compound. Most preferred is a chlorine atom-containing compound. The incorporated halogen atom-containing compound can be decomposed or converted into other halogen atom-containing compound in the course of the development of the reaction. The halogen atom-containing compound is generally employed in an amount of 0.001 to 300 moles, preferably 0.1 to 100 moles per one mole of the organic phosphorus compound.

The halogen atom-containing compound may be an inorganic compound or an organic compound.

Examples of the inorganic halogen atom-containing compounds are halides of aluminum (e.g., aluminum chloride and aluminum bromide), halides of metals belonging to the platinum group (e.g., platinum chloride, ruthenium chloride, palladium chloride, and chloroplatinic acid), halides of phosphorus (e.g., phosphorus trichloride, phosphorus pentachloride, phosphorus oxychloride, phosphorus tribromide, phosphorus pentabromide, and phosphorus oxybromide), hydrogen halides (e.g., hydrogen chloride and hydrogen bromide), halides of sulfur (e.g., thionyl chloride, sulfuryl chloride, sulfur dichloride, and disulfur dichloride), and halogens per se (e.g., chlorine and bromine).

The organic halogen atom-containing compound preferably contains (1) carbon atom, (2) a halogen atom such as chlorine atom or a bromine atom, and (3) at least one of other atoms selected from a hydrogen atom, a nitrogen atom, a sulfur atom, and a silicon atom.

Examples of the organic halogen atom-containing compounds are organic compounds having a C—Hal bonding (in which Hal means a halogen atom), a C—Si—Hal bonding, a C(O)—Hal bonding or a C—S(O)$_2$—Hal bonding. The organic halogen atom-containing compound can contain one or more halogen atoms such as chlorine(s), bromine(s) or iodine(s) singly or in combination.

Examples of the organic compounds having a C—Hal bonding include alkyl halides (e.g., chloroform, carbon tetrachloride, 1,2-dichloroethane, butyl chloride, and dodecyl chloride), aralkyl halides (e.g., benzyl chloride, benzotrichloride, triphenylmethyl chloride, and α-bromo-o-xylene), and halogenated aliphatic nitriles (e.g., β-chloropropionitrile, and γ-chlorobutyronitrile), halogenated aliphatic carboxylic acids (e.g., chloroacetic acid, bromoacetic acid, and chloropropionic acid).

Examples of the organic compounds having a C—Si—Hal bonding include halogenated silanes (e.g., diphenyldichlorosilane, and triphenylchlorosilane).

Examples of the organic compounds having a C(O)—Hal bonding include acyl halides (e.g., acetyl chloride, oxalyl chloride, propionyl chloride, stearoyl chloride, benzoyl chloride, 2-naphthalenecarboxylic acid chloride, and 2-thiophenecarboxylic acid chloride), halogenated formic acid aryl esters (e.g., phenyl chloroformate), and halogenated glyoxylic acid aryl esters (e.g., phenyl chloroglyoxylate).

Examples of the organic compounds having a C—S(O)$_2$—Hal bonding include sulfonyl chlorides (e.g., p-toluenesulfonic acid chloride, and 2-naphthalenesulfonic acid chloride).

The reaction for releasing CO from the diaryl oxalate according to the invention can be conducted at a temperature in the range of 100° to 450° C., preferably 160° to 450° C., more preferably 180° to 400° C., most preferably 180° to 350° C., in a reaction vessel in the presence of the organic phosphorus compound, and optionally in combination with the halogen atom-containing compound. In the course of progress of the reaction, carbon monoxide is emitted and the desired diaryl carbonate is formed. The reaction can be conducted under an atmospheric pressure, under a certain pressure, or under a reduced pressure. If the reaction temperature is higher than the reflux temperature of the starting diaryl oxalate, the reaction is preferably performed under pressure.

The decarbonylation reaction does not require any solvent. However, if necessary, an organic solvent which does not participate in the reaction can be employed. Such solvent can be diphenyl ether, sulforane, N-methylpyrrolidone, dimethylimidazolidone, or 1,3-dimethyl-3,4,5,6-tetrahydro-2(1H)-pyrimidinone.

The process for the preparation of a diaryl carbonate of the invention is characteristic in the use of an organic phosphorous compound as catalyst for decarbonylation reaction and is further characteristic in that the catalyst is repeatedly employed in the decarbonylation reaction.

The process of the invention comprises the steps of:

1) performing a decarbonylation reaction of a diaryl oxalate in the presence of an organic phosphorus compound catalyst to give a reaction mixture comprising a diaryl carbonate and the organic phosphorus compound catalyst—First decarbonylation;

2) recovering the diaryl carbonate from the reaction mixture—Product isolation; and 3) performing a decarbonylation reaction of a diaryl oxalate in the presence of the reaction mixture from which the diaryl carbonate has been recovered and to which a halogen atom-containing compound is added, to give a reaction mixture comprising a diaryl carbonate and the organic phosphorous compound catalyst—Second decarbonylation.

It is preferred that the second step (for product isolation) and the third step (for second decarbonylation) are repeated batchwithe or continuously in combination.

Figure 1:
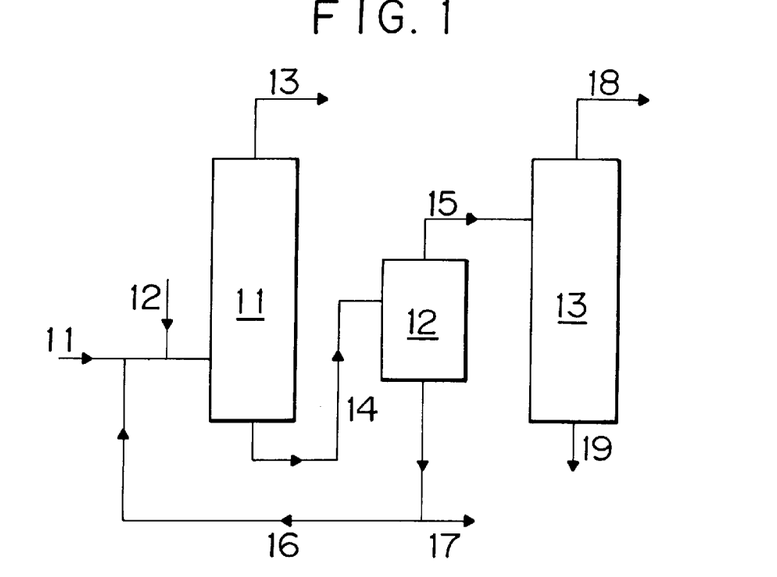

FIG. 1 shows a flow sheet to perform the above-mentioned preparation process.

In FIG. 1, the diaryl oxalate is introduced into a reactor 11 through a pipe line 11. The organic phosphorus compound catalyst (optionally, in combination with the halogen atom-containing compound) is supplied through a pipe line 12 to join the diaryl oxalate and incorporated into the reactor 11. In the reactor, the decarbonylation reaction proceeds, emitting carbon monoxide which is produced in the course of the decarbonylation reaction. The carbon monoxide is exhausted through a pipe line 13. The reaction mixture comprising a major portion of a diaryl carbonate (which is produced in the decarbonylation reaction), a small amount of the starting diaryl oxalate, and the catalyst composition is taken out from the bottom of the reactor through a pipe line 14, and introduced into an evaporator 12. In the evaporator, a distillate comprising a major portion of the diaryl carbonate is obtained and transferred through a pipe line 15 into a distillation tower 13. In the distillation tower, the diaryl carbonate is isolated to recover through a pipe line 18. The residue in the distillation tower is taken out through a pipe line 19.

A residue remaining in the evaporator is taken out from the evaporator. A portion of the residue is supplied into the pipe line 11 through a line 16 to join the diaryl oxalate to be supplied into the reactor 11. A remaining portion of the residue is removed through a pipe line 17.

The reactor can be utilized singly or in combination. The evaporator can be any one of known evaporators such as a film evaporator. The distillation tower preferably comprises a certain number (preferably 5 to 50) of theoretical plates.

One distillation tower can be employed in place of the combination of the evaporator and the distillation tower. The distillation can be performed at 150°–250° C. (for bottom temperature) and 80°–200° C., preferably 100°–180° C. (for top temperature) at a pressure of 2–100 mmHg.

The residue taken out from the evaporator can be in an amount of 1 to 20 wt. %, preferably 1 to 10 wt. % of the amount of the whole reaction mixture. The residue comprises almost all of the catalyst composition having been present in the reaction mixture, and small amounts of unreacted diaryl oxalate and produced diaryl carbonate. A portion of the residue can be removed from another portion to be recycled into the reactor, for obviating accumulation of by-products having a higher boiling point.

The second decarbonylation reaction can be performed using a mixture of a freshly supplied diaryl oxalate, the recycled residue comprising the catalyst composition, and a freshly supplied halogen atom-containing compound. If necessary, a fresh organic phosphorus compound is supplemented to compensate the catalyst portion such as that which has been exhausted through the pipeline 17 or decomposed.

If the organic phosphonium salt is employed as the organic phosphorus compound catalyst in the reaction for decarbonylation of a diaryl oxalate, the reaction mixture from which the diaryl carbonate has been recovered (removed) is preferably treated with an aqueous medium to recover the organic phosphonium salt, after the steps 2) and 3) are repeated in combination. Thus recovered organic phosphonium salt can be employed in the step 1) as the catalyst.

Figure 2:
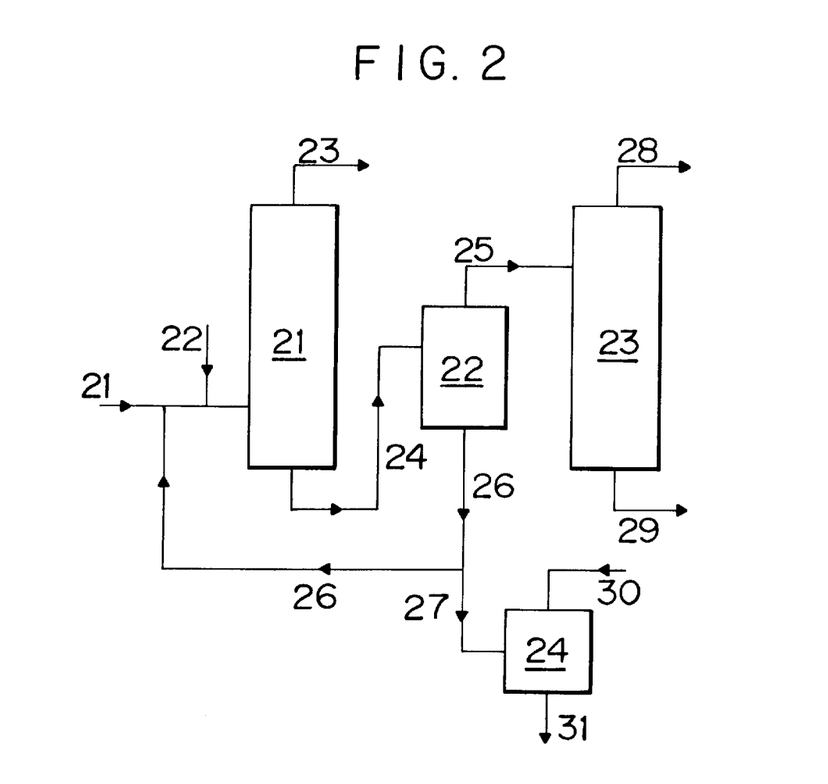

FIG. 2 shows a flow sheet to perform the process for the preparation of a diaryl carbonate which includes the recovery of the organic phosphonium salt using an aqueous medium.

In FIG. 2, the diaryl oxalate is introduced into a reactor 21 through a pipe line 21. The organic phosphonium salt catalyst (optionally, in combination with the halogen atom-containing compound) is supplied through a pipe line 22 to join the diaryl oxalate and incorporated into the reactor 21. In the reactor, the decarbonylation reaction proceeds, emitting carbon monoxide which is produced in the course of the decarbonylation reaction. The carbon monoxide is exhausted through a pipe line 23. The reaction mixture comprising a major portion of a diaryl carbonate (which is produced in the decarbonylation reaction), a small amount of the starting diaryl oxalate, and the catalyst composition is taken out from the bottom of the reactor through a pipe line 24, and introduced into an evaporator 22. In the evaporator, a distillate comprising a major portion of the diaryl carbonate is obtained and transferred through a pipe line 25 into a distillation tower 23. In the distillation tower, the diaryl carbonate is isolated to recover through a pipe line 28. The residue in the distillation tower is taken out through a pipe line 29.

A residue remaining in the evaporator is taken out from the evaporator. A portion of the residue is supplied into the pipe line 21 through a line 26 to join the diaryl oxalate to be supplied into the reactor 21. A remaining portion of the residue is removed through a pipe line 27 for treatment with an aqueous medium in a vessel 24.

Into the vessel 24, an aqueous medium such as water (preferably, deionized water) is supplied through a pipe line 30. In the vessel, the residue is treated with the aqueous medium in an amount of as much as 0.1 to 100 weight parts, preferably 1 to 50 weight parts, per one weight part of the residue to be treated. The aqueous mixture is stirred in the vessel to give a homogeneous slurry or suspension, so that the catalyst (i.e., organic phosphonium salt) is extracted into the aqueous portion. The aqueous portion is separated and taken out from the vessel through the pipe line 31. The organic phosphonium salt is then recovered from the aqueous portion.

The extraction procedure can be performed at a temperature from room temperature to the uppermost decarbonylation temperature. If the extraction is carried out at a temperature at which the residue is in a solid state, the aqueous mixture is preferably stirred at a high rate using a homogenizer. The extraction is performed generally for 5 min. to 1 hour, preferably 5 to 30 min. After the extraction procedure is complete, the resulting slurry or suspension is cooled to room temperature, if desired, and the insolubles are removed by filtration or centrifugal procedure. The aqueous portion is concentrated and heated to dryness. The heating is performed,for instance, at 120°–180° C. for 1–3 hours in a stream of an inert gas such as argon.

For the extraction, the aqueous medium can be employed in combination with an organic solvent such as an aromatic hydrocarbon (e.g., toluene) or a halogenated aliphatic hydrocarbon (e.g., chloroform, methylene chloride, and 1,2-dichloroethane) in an amount of 0.01 to 100 volume parts, preferably 0.1 to 10 volume parts, per one volume part of the aqueous medium such as water. The organic solvent can be easily removed in a vessel after the extraction is complete.

The second decarbonylation reaction can be performed using a mixture of a freshly supplied diaryl oxalate, the recovered organic phosphonium salt catalyst (if desired, in combination with the residue comprising the organic phosphonium salt which is recycled through the line 26, and a freshly supplied halogen atom-containing compound. If necessary, a fresh organic phosphonium salt is supplemented.

The present invention is further described by the following examples. In the examples, the "conversion ratio of diaryl oxalate" (i.e., ratio of amount of consumed (or reacted) diaryl oxalate per the amount of charged diaryl oxalate and "selectivity to diaryl carbonate" (i.e., ratio of the amount of produced diaryl carbonate per the amount of consumed diaryl oxalate) for decarbonylation reaction of the diaryl oxalate are all expressed in terms of molar percent ratio (i.e., mol. %).

EXAMPLE 1

In a 100 mL-volume glass flask equipped with a thermometer and a reflux condenser, a mixture of diphenyl oxalate (41.32 mmol.), tetraphenylphosphonium chloride (catalyst, 0.825 mmol.: 2.0 molar % per the amount of diphenyl oxalate) and chloroform ($CHCl_3$, 0.2 mol. per one mol. of catalyst) was heated under stirring to 230° C. for 2 hours. The decarbonylation reaction was carried out at an atmospheric pressure, removing emitted carbon monoxide from the reaction mixture. The tetraphenylphosphonium chloride was heated at 120° C. for one hour, 150° C. for one hour, and 180° C. for one hour in a stream of a dry argon gas, and cooled to room temperature also in a stream of an argon gas, before it was employed for the above decarbonylation reaction.

After the reaction was complete, the reaction mixture was analyzed by gas chromatography to indicate 95.4% of the conversion ratio of diphenyl oxalate (DPO con.) and 99.0% of the selectivity to diphenyl carbonate (DPC sel.).

The reaction mixture was distilled under reduced pressure (2–3 mmHg/185° C., bath temperature) to recover the produced diphenyl carbonate. The amount of the distillate was 90 wt. % of the reaction mixture. The residue was subjected to the second decarbonylation reaction in the same manner after the same amounts of diphenyl oxalate and chloroform were added.

The same decarbonylation reaction was repeated as many as 6 times (total) in the same manner. The results are set forth in Table 1.

TABLE 1

| Run No. | DPO (mmol) | Chloroform (molar ratio) | DPO con. (%) | DPC. sel. (%) |
|---|---|---|---|---|
| 1 | 41.32 | 0.2 | 95.4 | 99.0 |
| 2 | 41.32 | 0.2 | 97.0 | 99.0 |
| 3 | 41.32 | 0.2 | 95.8 | 99.0 |
| 4 | 41.32 | 0.2 | 93.4 | 99.0 |
| 5 | 41.32 | 0.2 | 95.0 | 99.0 |
| 6 | 41.32 | 0.2 | 96.1 | 99.0 |

Remarks: DPO: diphenyl oxalate, DPC: diphenyl carbonate

The molar ratio of chloroform is based on the catalyst amount.

EXAMPLE 2

In a 50 mL-volume glass flask equipped with a thermometer and a reflux condenser, a mixture of diphenyl oxalate (20.83 mmol.), tetraphenylphosphonium chloride (catalyst, 0.10 mmol.: 0.5 molar % per the amount of diphenyl oxalate) and oxalyl chloride (0.6 mol. per one mol. of catalyst) was heated under stirring to 255° C. for 1 hour. The decarbonylation reaction was carried out at an atmospheric pressure, removing emitted carbon monoxide from the reaction mixture.

After the reaction was complete, the reaction mixture was analyzed by gas chromatography to indicate 85.0% of the conversion ratio of diphenyl oxalate (DPO con.) and 99.0% of the selectivity to diphenyl carbonate (DPC sel.).

The reaction mixture was treated in the same manner as in Example 1 to employ the residual catalyst repeatedly in the following decarbonylation reactions as many as 29 times (total) in the same manner. The results are set forth in Table 2.

TABLE 2

| Run No. | DPO (mmol) | Oxalyl Chloride (molar ratio) | DPO con. (%) | DPC. sel. (%) |
|---|---|---|---|---|
| 1 | 20.83 | 0.6 | 85.0 | 99.0 |
| 2 | 20.83 | 0.6 | 85.6 | 99.0 |
| 3 | 20.83 | 0.6 | 85.1 | 99.0 |
| 4 | 20.83 | 0.6 | 84.8 | 99.0 |
| 5 | 20.83 | 0.6 | 86.0 | 99.0 |
| 6 | 20.83 | 0.6 | 85.0 | 99.0 |
| 7 | 20.83 | 0.6 | 94.6 | 99.0 |
| 8 | 20.83 | 0.6 | 91.6 | 99.0 |
| 9 | 20.83 | 0.6 | 89.0 | 99.0 |
| 10 | 20.83 | 0.6 | 85.5 | 99.0 |
| 11 | 20.83 | 0.6 | 79.2 | 99.0 |
| 12 | 20.83 | 0.6 | 88.2 | 99.0 |
| 13 | 20.83 | 0.6 | 81.3 | 99.0 |
| 14 | 20.83 | 0.6 | 78.3 | 99.0 |
| 15 | 20.83 | 0.6 | 83.5 | 99.0 |
| 16 | 20.83 | 0.6 | 86.0 | 99.0 |
| 17 | 20.83 | 0.6 | 84.4 | 99.0 |
| 18 | 20.83 | 0.6 | 79.1 | 99.0 |
| 19 | 20.83 | 0.6 | 76.4 | 99.0 |
| 20 | 20.83 | 0.6 | 93.6 | 99.0 |
| 21 | 20.83 | 0.6 | 89.4 | 99.0 |
| 22 | 20.83 | 0.6 | 83.2 | 99.0 |

TABLE 2-continued

| Run No. | DPO (mmol) | Oxalyl Chloride (molar ratio) | DPO con. (%) | DPC. sel. (%) |
|---|---|---|---|---|
| 23 | 20.83 | 0.6 | 87.3 | 99.0 |
| 24 | 20.83 | 0.6 | 77.2 | 99.0 |
| 25 | 20.83 | 0.6 | 84.4 | 99.0 |
| 26 | 20.83 | 0.6 | 79.3 | 99.0 |
| 27 | 20.83 | 0.6 | 87.8 | 99.0 |
| 28 | 20.83 | 0.6 | 88.2 | 99.0 |
| 29 | 20.83 | 0.6 | 82.6 | 99.0 |

EXAMPLE 3

The procedures of Example 2 were repeated except that 20.58 mmol. of diphenyl oxalate and 0.092 mmol. (0.45 molar % based on the amount of diphenyl oxalate) of tetraphenylphosphonium hydrogen dichloride (catalyst) were used, that the reaction temperature was changed into 260° C. and that no oxalyl chloride was employed.

The tetraphenylphosphonium hydrogen dichloride was prepared in the manner described in Z. anorg. allg. Chem., 551(1987), 179.

After the reaction was complete, the reaction mixture was analyzed by gas chromatography to indicate 89.7% of the conversion ratio of diphenyl oxalate (DPO con.) and 99.0% of the selectivity to diphenyl carbonate (DPC sel.).

The reaction mixture was treated in the same manner as in Example 1 to employ the residual catalyst repeatedly and chloroform (1.4 mol. per 1 mol. of catalyst) in the following decarbonylation reactions as many as 6 times (total) in the same manner. The results are set forth in Table 3.

TABLE 3

| Run No. | DPO (mmol) | Chloroform (molar ratio) | DPO con. (%) | DPC. sel. (%) |
|---|---|---|---|---|
| 1 | 20.58 | — | 89.7 | 99.0 |
| 2 | 20.58 | 1.4 | 89.2 | 99.0 |
| 3 | 20.58 | 1.4 | 85.7 | 99.0 |
| 4 | 20.58 | 1.4 | 93.6 | 99.0 |
| 5 | 20.58 | 1.4 | 93.1 | 99.0 |
| 6 | 20.58 | 1.4 | 92.2 | 99.0 |

EXAMPLE 4

The procedures of Example 2 were repeated except that 7.88 mmol. of diphenyl oxalate and 0.039 mmol. (0.5 molar % based on the amount of diphenyl oxalate) of tetraphenylphosphonium chloride (catalyst) were used, that oxalyl chloride was replaced with chloroacetic acid (2.0 mol. per one mole of catalyst), and that the reaction temperature was changed into 260° C.

After the reaction was complete, the reaction mixture was analyzed by gas chromatography to indicate 81.4% of the conversion ratio of diphenyl oxalate (DPO con.) and 99.0% of the selectivity to diphenyl carbonate (DPC sel.).

The reaction mixture was treated in the same manner as in Example 1 in the following decarbonylation reactions as many as 2 times (total) in the same manner. The results are set forth in Table 4.

EXAMPLE 5

The procedures of Example 2 were repeated except that 7.97 mmol. of diphenyl oxalate and 0.040 mmol. (0.5 molar % based on the amount of diphenyl oxalate) of tetraphenylphosphonium chloride (catalyst) were used, that oxalyl chloride was replaced with 3-chloro-1-propene (2.6 mol. per one mole of catalyst), and that the reaction temperature was changed into 260° C.

After the reaction was complete, the reaction mixture was analyzed by gas chromatography to indicate 82.6% of the conversion ratio of diphenyl oxalate (DPO con.) and 99.0% of the selectivity to diphenyl carbonate (DPC sel.).

The reaction mixture was treated in the same manner as in Example 1 in the following decarbonylation reactions as many as 2 times (total) in the same manner. The results are set forth in Table 4.

EXAMPLE 6

The procedures of Example 2 were repeated except that 12.39 mmol. of diphenyl oxalate and 0.061 mmol. (0.5 molar % based on the amount of diphenyl oxalate) of tetraphenylphosphonium chloride (catalyst) were used, that oxalyl chloride was replaced with 1-chlorohexane (one mole per one mole of catalyst), and that the reaction temperature was changed into 260° C.

After the reaction was complete, the reaction mixture was analyzed by gas chromatography to indicate 90.8% of the conversion ratio of diphenyl oxalate (DPO con.) and 99.0% of the selectivity to diphenyl carbonate (DPC sel.).

The reaction mixture was treated in the same manner as in Example 1 in the following decarbonylation reactions as many as 2 times (total) in the same manner. The results are set forth in Table 4.

EXAMPLE 7

The procedures of Example 2 were repeated except that 8.23 mmol. of diphenyl oxalate and 0.041 mol. (0.5 molar % based on the amount of diphenyl oxalate) of tetraphenylphosphonium chloride (catalyst) were used, that oxalyl chloride was replaced with benzoyl chloride (3.6 mol. per one mole of catalyst), and that the reaction temperature was changed into 260° C.

After the reaction was complete, the reaction mixture was analyzed by gas chromatography to indicate 89.8% of the conversion ratio of diphenyl oxalate (DPO con.) and 99.0% of the selectivity to diphenyl carbonate (DPC sel.).

The reaction mixture was treated in the same manner as in Example 1 in the following decarbonylation reactions as many as 2 times (total) in the same manner. The results are set forth in Table 4.

EXAMPLE 8

The procedures of Example 2 were repeated except that 41.29 mmol. of diphenyl oxalate and 0.826 mmol. (2.0 molar % based on the amount of diphenyl oxalate) of tetraphenylphosphonium chloride (catalyst) were used, that oxalyl chloride was replaced with gaseous hydrogen chloride (3.0 mol. per one mole of catalyst, supplied during the initial 30 minutes from the beginning of the reaction: after diluted with nitrogen gas to give 1 vol. % HCl concentration), and that the reaction temperature was changed into 230° C.

After the reaction was complete, the reaction mixture was analyzed by gas chromatography to indicate 80.1% of the conversion ratio of diphenyl oxalate (DPO con.) and 99.0% of the selectivity to diphenyl carbonate (DPC sel.).

The reaction mixture was treated in the same manner as in Example 1 in the following decarbonylation reactions as many as 2 times (total) in the same manner. The results are set forth in Table 4.

Comparison Example 1

The procedures of Example 1 were repeated except for employing no chloroform.

After the reaction was complete, the reaction mixture was analyzed by gas chromatography to indicate 93.4% of the conversion ratio of diphenyl oxalate (DPO con.) and 99.0% of the selectivity to diphenyl carbonate (DPC sel.).

The reaction mixture was treated in the same manner as in Example 1 in the following decarbonylation reactions as many as 3 times (total) in the same manner. The results are set forth in Table 4.

TABLE 4

| Run No. | DPO (mmol) | Halogen compound (molar ratio) | DPO con. (%) | DPC. sel. (%) |
|---|---|---|---|---|
| Example 4 (Halogen compound: chloroacetic acid) | | | | |
| 1 | 7.88 | 2.0 | 81.4 | 99.0 |
| 2 | 7.88 | 2.0 | 80.5 | 99.0 |
| Example 5 (Halogen compound: 3-chloro-1-propene) | | | | |
| 1 | 7.97 | 2.6 | 82.6 | 99.0 |
| 2 | 7.97 | 2.6 | 81.0 | 99.0 |
| Example 6 (Halogen compound: 1-chlorohexane) | | | | |
| 1 | 12.39 | 1.0 | 90.8 | 99.0 |
| 2 | 12.39 | 1.0 | 89.6 | 99.0 |
| Example 7 (Halogen compound: benzoyl chloride) | | | | |
| 1 | 8.23 | 3.6 | 89.8 | 99.0 |
| 2 | 8.23 | 3.6 | 87.0 | 99.0 |
| Example 8 (Halogen compound: hydrogen chloride) | | | | |
| 1 | 41.29 | 3.0 | 80.1 | 99.0 |
| 2 | 41.29 | 3.0 | 79.9 | 99.0 |
| Comparison Example 1 (Halogen compound: none) | | | | |
| 1 | 41.32 | — | 93.4 | 99.0 |
| 2 | 41.32 | — | 55.4 | 99.0 |
| 3 | 41.32 | — | 36.8 | 53.2 |

EXAMPLE 9

The procedures of Example 2 were repeated except that 18.81 mmol. of diphenyl oxalate and 0.376 mmol. (2.0 molar % based on the amount of diphenyl oxalate) of tetraphenylphosphonium bromide (catalyst) were used, that oxalyl chloride was replaced with chloroform (2.0 mol. per one mole of catalyst), and that the reaction temperature and the reaction period were changed into 230° C. and 2 hours, respectively. After the reaction was complete, the reaction mixture was analyzed by gas chromatography to indicate 76.8% of the conversion ratio of diphenyl oxalate (DPO con.) and 97.6% of the selectivity to diphenyl carbonate (DPC sel.).

The reaction mixture was treated in the same manner as in Example 1 in the following decarbonylation reactions as many as 2 times (total) in the same manner. The results are set forth in Table 5.

EXAMPLE 10

The procedures of Example 2 were repeated except that 21.27 mmol. of diphenyl oxalate and 1.504 mmol. (7.0 molar % based on the amount of diphenyl oxalate) of triphenylphosphine (catalyst) were used, that oxalyl chloride was replaced with chloroform (one mole per one mole of catalyst), and that the reaction temperature and the reaction period were changed into 250° C. and 2 hours, respectively.

After the reaction was complete, the reaction mixture was analyzed by gas chromatography to indicate 58.5% of the conversion ratio of diphenyl oxalate (DPO con.) and 91.4% of the selectivity to diphenyl carbonate (DPC sel.).

The reaction mixture was treated in the same manner as in Example 1 in the following decarbonylation reactions as many as 2 times (total) in the same manner. The results are set forth in Table 5.

EXAMPLE 11

The procedures of Example 2 were repeated except that 20.75 mmol. of diphenyl oxalate and 1.038 mmol. (5.0 molar % based on the amount of diphenyl oxalate) of triphenylphosphine oxide (catalyst) were used, that oxalyl chloride was replaced with chloroform (one mole per one mole of catalyst), and that the reaction temperature and the reaction period were changed into 250° C. and 2 hours, respectively.

After the reaction was complete, the reaction mixture was analyzed by gas chromatography to indicate 34.6% of the conversion ratio of diphenyl oxalate (DPO con.) and 77.8% of the selectivity to diphenyl carbonate (DPC sel.).

The reaction mixture was treated in the same manner as in Example 1 in the following decarbonylation reactions as many as 2 times (total) in the same manner. The results are set forth in Table 5.

EXAMPLE 12

The procedures of Example 2 were repeated except that 20.81 mmol. of diphenyl oxalate and 1.069 mmol. (5.1 molar % based on the amount of diphenyl oxalate) of triphenylphosphine dichloride (catalyst) were used, that oxalyl chloride was replaced with chloroform (0.9 mol. per one mole of catalyst), and that the reaction temperature and the reaction period were changed into 250° C. and 2 hours, respectively.

After the reaction was complete, the reaction mixture was analyzed by gas chromatography to indicate 99.1% of the conversion ratio of diphenyl oxalate (DPO con.) and 99.0% of the selectivity to diphenyl carbonate (DPC sel.).

The reaction mixture was treated in the same manner as in Example 1 in the following decarbonylation reactions as many as 2 times (total) in the same manner. The results are set forth in Table 5.

TABLE 5

| Run No. | DPO (mmol) | Chloroform (molar ratio) | DPO con. (%) | DPC. sel. (%) |
|---|---|---|---|---|
| Example 9 (Catalyst: tetraphenylphosphonium bromide) | | | | |
| 1 | 18.81 | 3.3 | 76.8 | 97.6 |
| 2 | 18.81 | 3.3 | 94.6 | 99.0 |
| Example 10 (Catalyst: triphenylphosphine) | | | | |
| 1 | 21.27 | 1.0 | 58.5 | 91.4 |
| 2 | 21.27 | 1.0 | 59.7 | 85.2 |
| Example 11 (Catalyst: triphenylphosphine oxide) | | | | |
| 1 | 20.75 | 1.0 | 34.6 | 77.8 |
| 2 | 20.75 | 1.0 | 39.0 | 73.1 |
| Example 12 (Catalyst: triphenylphosphine dichloride) | | | | |
| 1 | 20.81 | 0.9 | 99.0 | 99.0 |
| 2 | 20.81 | 0.9 | 81.3 | 89.9 |

EXAMPLE 13

In a 50 mL-volume glass flask equipped with a thermometer and a reflux condenser, a mixture of diphenyl oxalate (10.010 g, 41.23 mmol.), tetraphenylphosphonium chloride (catalyst, 0.3090 g, 0.825 mmol.: 2.0 molar % per the amount of diphenyl oxalate) and chloroform (0.195 g) was heated under stirring to 230° C. for 2 hour.

The decarbonylation reaction was carried out at an atmospheric pressure, removing emitted carbon monoxide from the reaction mixture. The tetraphenylphosphonium chloride was heated at 120° C. for one hour, 150° C. for one hour, and 180° C. for one hour in a stream of a dry argon gas, and cooled to room temperature also in a stream of an argon gas, before it was employed for the above decarbonylation reaction.

After the reaction was complete, the reaction mixture was analyzed by gas chromatography to indicate 95.4% of the conversion ratio of diphenyl oxalate (DPO con.) and 99.0% of the selectivity to diphenyl carbonate (DPC sel.).

The reaction mixture was distilled under reduced pressure (2–3 mmHg/185° C., bath temperature) to recover the produced diphenyl carbonate. The amount of the distillate was 90 wt. % of the reaction mixture. The residue was subjected to the second decarbonylation reaction in the same manner after the same amounts of diphenyl oxalate and chloroform were added.

The same decarbonylation reaction was repeated as many as 5 times (total) in the same manner.

The reaction mixture produced after the 5 times run were performed was distilled under reduced pressure (2–3 mmHg/160° C., bath temperature) to recover the produced diphenyl carbonate. The amount of the distillate was 90 wt. % of the reaction mixture.

The residue was cooled to room temperature, and stirred at room temperature for 10 minutes in a homogenizer after addition of 50 mL of deionized water. The homogenized aqueous mixture was filtered using suction and the filtrate was concentrated to give a solid. The solid was heated under reduced pressure (130° C., 3 hours) to obtain 0.3062 g of tetraphenylphosphonium chloride (recovery yield: 99.1%).

The obtained tetraphenylphosphonium chloride was subjected to the sixth decarbonylation reaction in the same manner after the same amounts of diphenyl oxalate and chloroform were added.

The results are set forth in Table 6.

TABLE 6

| Run No. | DPO (mmol) | Chloroform (molar ratio) | DPO con. (%) | DPC. sel. (%) |
|---|---|---|---|---|
| 1 | 41.32 | 0.0195 | 95.4 | 99.0 |
| 2 | 41.32 | 0.0195 | 97.0 | 99.0 |
| 3 | 41.32 | 0.0195 | 95.8 | 99.0 |
| 4 | 41.32 | 0.0195 | 93.4 | 99.0 |
| 5 | 41.32 | 0.0195 | 95.0 | 99.0 |
| 6 | 41.32 | 0.0195 | 95.2 | 99.0 |

EXAMPLE 14

The procedures of Example 13 were repeated except that chloroform was replaced with oxalyl chloride (0.0207 g). The procedures were repeated as many as 5 times (total). After the 5th run, the tetraphenylphosphonium chloride was recovered from an aqueous mixture in the same manner as in Example 13. Then, the sixth run was performed in the same manner.

The results are set forth in Table 7.

TABLE 7

| Run No. | DPO (mmol) | Oxalyl Chloride (molar ratio) | DPO con. (%) | DPC. sel. (%) |
|---|---|---|---|---|
| 1 | 41.32 | 0.0207 | 95.3 | 99.0 |
| 2 | 41.32 | 0.0207 | 94.8 | 99.0 |
| 3 | 41.32 | 0.0207 | 95.2 | 99.0 |
| 4 | 41.32 | 0.0207 | 95.3 | 99.0 |
| 5 | 41.32 | 0.0207 | 95.1 | 99.0 |
| 6 | 41.32 | 0.0207 | 95.0 | 99.0 |

EXAMPLE 15

The procedures of Example 13 were repeated except that the amounts of diphenyl oxalate, tetraphenylphosphonium chloride, and chloroform were changed to 10.045 g (41.47 mmol.), 0.4612 g (1.230 mmol., 3.0 molar % based on the amount of diphenyl oxalate), and 0.037 g, respectively.

After the reaction was complete, the reaction mixture was analyzed by gas chromatography to indicate 99.5% of the conversion ratio of diphenyl oxalate (DPO con.) and 99.0% of the selectivity to diphenyl carbonate (DPC sel.).

The produced reaction mixture was distilled under reduced pressure in the same manner as in Example 13 to recover the produced diphenyl carbonate. The amount of the distillate was 90 wt. % of the reaction mixture.

The residue was cooled to room temperature, and stirred after addition of 50 mL of deionized water in the same manner as in Example 13, to obtain 0.4589 g of tetraphenylphosphonium chloride (recovery yield: 99.5%).

The obtained tetraphenylphosphonium chloride was subjected to the second decarbonylation reaction in the same manner after the same amounts of diphenyl oxalate and chloroform were added.

The procedures were repeated as many as 6 times (total). After the 5th run, the tetraphenylphosphonium chloride was recovered from an aqueous mixture in the same manner as in Example 13. Then, the sixth run was performed in the same manner. The results are set forth in Table 8.

TABLE 8

| Run No. | DPO (mmol) | Chloroform (molar ratio) | DPO con. (%) | DPC. sel. (%) |
|---|---|---|---|---|
| 1 | 41.47 | 0.037 | 95.5 | 99.0 |
| 2 | 41.47 | 0.037 | 99.5 | 99.0 |
| 3 | 41.47 | 0.037 | 99.4 | 99.0 |
| 4 | 41.47 | 0.037 | 99.5 | 99.0 |
| 5 | 41.47 | 0.037 | 99.4 | 99.0 |
| 6 | 41.47 | 0.037 | 99.4 | 99.0 |
| 6 | 41.32 | 0.037 | 99.4 | 99.0 |

EXAMPLE 16

The procedures of Example 15 were repeated except that the period for stirring the aqueous mixture was changed into 5 minutes to recover 0.04557 g of tetraphenylphosphonium chloride (recovery yield: 98.8%).

The obtained tetraphenylphosphonium chloride was subjected to the second decarbonylation reaction in the same manner after the same amounts of diphenyl oxalate and chloroform were added.

After the reaction was complete, the reaction mixture was analyzed to indicate 99.5% of the conversion ratio of diphenyl oxalate (DPO con.) and 99.0% of the selectivity to diphenyl carbonate (DPC sel.).

EXAMPLE 17

The procedures of Example 15 were repeated except that the deionized water (50 mL) was replaced with a combination of 30 mL of deionized water and 30 mL of toluene to recover 0.04391 g of tetraphenylphosphonium chloride (recovery yield: 95.2%). The separation of the aqueous portion was performed using a separatory funnel.

The obtained tetraphenylphosphonium chloride was subjected to the second decarbonylation reaction in the same manner after the same amounts of diphenyl oxalate and chloroform were added.

After the reaction was complete, the reaction mixture was analyzed to indicate 99.5% of the conversion ratio of diphenyl oxalate (DPO con.) and 99.0% of the selectivity to diphenyl carbonate (DPC sel.).

EXAMPLE 18

The procedures of Example 13 were repeated except that the amounts of diphenyl oxalate and tetraphenylphosphonium chloride were changed to 10.003 g (41.29 mmol.) and 0.3102 g (0.826 mmol., 2.0 molar % based on the amount of diphenyl oxalate), respectively and that chloroform was replaced with 0.090 g gaseous hydrogen chloride (which was diluted with nitrogen gas to give 1 vol. % HCl concentration).

After the reaction was complete, the reaction mixture was analyzed to indicate 93.7% of the conversion ratio of diphenyl oxalate (DPO con.) and 99.0%. of the selectivity to diphenyl carbonate (DPC sel.).

The reaction mixture was distilled under reduced pressure to recover the produced diphenyl carbonate in the same manner as in Example 13. The residue was subjected to the second decarbonylation reaction in the same manner after the same amounts of diphenyl oxalate and hydrogen chloride were added.

The same decarbonylation reaction was repeated as many as 5 times (total) in the same manner.

The reaction mixture produced after the 5 times run were performed was distilled to recover the produced diphenyl carbonate. The amount of the distillate was 90 wt. % of the reaction mixture.

The residue was cooled to room temperature, and stirred at room temperature for 10 minutes in a homogenizer after addition of 50 mL of deionized water. The homogenized aqueous mixture was then treated in the same manner to obtain 0.308 g of tetraphenylphosphonium chloride (recovery yield: 99.1%).

The obtained tetraphenylphosphonium chloride was subjected to the sixth decarbonylation reaction in the same manner after the same amounts of diphenyl oxalate and hydrogen chloride were added.

The results are set forth in Table 9.

TABLE 9

| Run No. | DPO (mmol) | HCL (g) | DPO con. (%) | DPC. sel. (%) |
|---|---|---|---|---|
| 1 | 41.29 | 0.090 | 93.7 | 99.0 |
| 2 | 41.29 | 0.090 | 93.2 | 99.0 |
| 3 | 41.29 | 0.090 | 93.4 | 99.0 |
| 4 | 41.29 | 0.090 | 92.9 | 99.0 |
| 5 | 41.29 | 0.090 | 93.3 | 99.0 |
| 6 | 41.29 | 0.090 | 93.0 | 99.0 |

What is claimed is:

1. A process for preparing a diaryl carbonate from a diaryl oxalate in a liquid phase by decarbonylation which comprises the steps of:
   1) performing a decarbonylation reaction of a diaryl oxalate in the presence of an organic phosphorus compound catalyst to give a reaction mixture comprising a diaryl carbonate and the organic phosphorus compound catalyst;
   2) recovering the diaryl carbonate from the reaction mixture; and
   3) performing a decarbonylation reaction of a diaryl oxalate in the presence of the reaction mixture from which the diaryl carbonate has been recovered and to which a halogen atom-containing compound is added, to give a reaction mixture comprising a diaryl carbonate and the organic phosphorous compound catalyst.

2. The process of claim 1, wherein the steps 2) and 3) is repeated in combination.

3. The process of claim 1, wherein the organic phosphorus compound catalyst comprises a compound having a trivalent or pentavalent phosphorus atom and at least one carbon-phosphorus bonding.

4. The process of claim 1, wherein the catalyst comprises a compound selected from the group consisting of an organic phosphonium compound, a phosphine, a phosphine dihalide, and a phosphine oxide.

5. The process of claim 1, wherein the catalyst comprises a compound selected from the group consisting of a tetraarylphosphonium salt, a triarylphosphine, a triarylphosphine dihalide and a triarylphosphine oxide.

6. The process of claim 1, wherein the catalyst comprises a compound selected from the group consisting of a tetraarylphosphonium halide and a tetraarylphosphonium hydrogen dihalide.

7. The process of claim 1, wherein the halogen atom-containing compound is an organic halogen atom-containing compound having a chemical structure in which a halogen atom is bonded to a carbon atom having thereon no double bond other than =O.

8. The process of claim 1, wherein the halogen atom-containing compound is an inorganic halogen atom-containing compound selected from the group consisting of a halide of phosphorus, a halide of sulfur, a hydrogen halide, and a halogen.

9. The process of claim 1, wherein the halogen atom-containing compound is a chlorine-containing compound.

10. The process of claim 1, wherein the organic phosphorus compound catalyst comprises an organic phosphonium salt; the reaction mixture from which the diaryl carbonate has been recovered is treated with an aqueous medium to recover the organic phosphonium salt; and the recovered organic phosphonium salt is employed in the step 1) as the catalyst.

11. The process of claim 1, wherein the organic phosphorus compound catalyst comprises an organic phosphonium salt; after the steps 2) and 3) are repeated in combination, the reaction mixture from which the diaryl carbonate has been recovered is treated with an aqueous medium to recover the organic phosphonium salt; and the recovered organic phosphonium salt is employed in the step 1) as the catalyst.

* * * * *